United States Patent
Cazzini (10) Patent No.: US 7,618,177 B2
(45) Date of Patent: Nov. 17, 2009

(54) MULTI-FIBER VARIABLE INTENSITY WIDE-ANGLE ILLUMINATOR

(75) Inventor: Karl Cazzini, Orchard Park, NY (US)

(73) Assignee: Alcon, Inc., Fort Worth, TX (US)

( * ) Notice: Subject to any disclaimer, the term of this patent is extended or adjusted under 35 U.S.C. 154(b) by 244 days.

(21) Appl. No.: 11/410,419

(22) Filed: Apr. 25, 2006

(65) Prior Publication Data

US 2006/0245702 A1    Nov. 2, 2006

Related U.S. Application Data

(60) Provisional application No. 60/676,201, filed on Apr. 29, 2005.

(51) Int. Cl.
*A61B 1/06*    (2006.01)
(52) U.S. Cl. .................. 362/572; 362/573; 362/551; 362/556; 362/804; 362/575
(58) Field of Classification Search .............. 362/572, 362/551, 554, 556, 573, 574, 575, 804; 600/249; 606/3, 10–12
See application file for complete search history.

(56) References Cited

U.S. PATENT DOCUMENTS

| 4,772,093 A | 9/1988 | Abele et al. |
| 5,058,985 A * | 10/1991 | Davenport et al. .......... 385/115 |
| 5,624,438 A | 4/1997 | Turner |
| 5,725,514 A | 3/1998 | Grinblat et al. |
| 6,254,530 B1 | 7/2001 | Ryan |

FOREIGN PATENT DOCUMENTS

EP    1 522 290 A1    4/2005

* cited by examiner

*Primary Examiner*—Sandra L O'Shea
*Assistant Examiner*—Jessica L McMillan
(74) *Attorney, Agent, or Firm*—Armando Pastrana, Jr.

(57) ABSTRACT

An illuminator and surgical illumination system are disclosed, one embodiment of the surgical illumination system comprising: a light source for providing a light beam; an optical cable, optically coupled to the light source for receiving and transmitting the light beam; a handpiece operably coupled to the optical cable; an optical fiber assembly operably coupled to the handpiece, wherein the optical fiber assembly is optically coupled to the optical cable to receive and transmit the light beam and wherein the optical fiber assembly comprises a plurality of fiber guides, wherein each fiber guide comprises a cladding having one or more fiber cores for transmitting and scattering the light beam to illuminate the surgical field, and a cannula, operably coupled to the handpiece for housing and directing the optical fiber assembly. The surgical illumination system can further comprise a separator operable to maintain a spacing between the fiber guides.

37 Claims, 5 Drawing Sheets

MULTI-FIBER VARIABLE INTENSITY WIDE-ANGLE ILLUMINATOR

CROSS-REFERENCE TO RELATED APPLICATIONS

This application claims priority under 35 U.S.C. §119 to U.S. Provisional Patent Application No. 60/676,201, filed Apr. 29, 2005, the entire contents of which are incorporated herein by reference.

TECHNICAL FIELD OF THE INVENTION

The present invention relates generally to surgical instrumentation. In particular, the present invention relates to surgical instruments for illuminating an area during surgery. Even more particularly, the present invention relates to a variable intensity, small gauge, wide-angle illuminator for illumination of a surgical field.

BACKGROUND OF THE INVENTION

In ophthalmic surgery, and, in particular, in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems. Currently existing wide-angle illuminators, however, display several disadvantages.

One disadvantage exhibited by some prior art wide-angle illuminators for ophthalmic surgery is a matching of the light refracting index of the vitreous eye fluid to that of the light refracting surface of the lens of the illuminator that comes in contact with the vitreous eye fluid. Contact of the vitreous eye fluid with the light refracting surface of the light spreading lens of such prior art systems results in sub-optimal light refraction due to index switching caused by the vitreous eye fluid. U.S. Pat. No. 5,624,438, entitled "Retinal Wide-Angle Illuminator For Eye Surgery," and issued to R. Scott Turner, provides a system for overcoming the effect of refractive index matching through the use of a high refractive-index step, mediated by the presence of an air-gap. The air-gap is presented between the distal end of an optical fiber and the light refracting surface of the illuminator lens. The light emanating from the optical wave guide (i.e., the optical fiber) will therefore undergo angular dispersion without any index switching that might be caused by contact with the vitreous eye fluid before it passes through the light refracting surface of the illuminator lens.

Another disadvantage of currently available wide-angle illuminators is glare. Glare results when the source of the illumination is small and bright, and the user (e.g., an ophthalmic surgeon) has a direct line of sight to the small bright illumination source. Glare is unwanted stray radiation that provides no useful illumination, and either distracts an observer or obscures an object under observation. Glare can be corrected for in current wide-angle illuminators, but typically only by reducing the total illumination light flux, which reduces the amount of light available for observation by the surgeon. For example, the "bullet probe" manufactured by Alcon Laboratories, Inc., of Fort Worth, Tex., achieves wide-angle illumination by using a bullet-shaped fiber having a surface diffusive finish to scatter light emanating from the distal end of an optical fiber. To reduce glare, the bullet probe can use a geometric shield, which reduces the illumination angle by reducing the overall available light flux.

A further disadvantage of typical prior art wide-angle illuminators is that they do not provide for varying the illumination angle and/or the intensity of the light source to adjust illumination for different conditions within the surgical field. Further still, prior art wide-angle surgical illuminators are expensive to produce, a cost which is passed along to the surgeon and ultimately to the patient. As a result, prior art illuminators are typically not disposable and will require periodic maintenance and sterilization between surgical procedures.

Therefore, a need exists for a variable-intensity, wide-angle illuminator that can reduce or eliminate the problems of refractive-index matching, glare, adjustable illumination properties, cost, efficiency and other problems associated with prior art wide-angle illuminators.

BRIEF SUMMARY OF THE INVENTION

The embodiments of the multi-fiber variable intensity wide-angle illuminator of the present invention substantially meet these needs and others. The various embodiments of the present invention provide for a reusable and for a disposable small gauge (e.g., 19, 20 or 25 gauge) optical fiber based endo-illuminator device for use in a surgical environment, such as vitreo-retinal/posterior segment surgery. Embodiments of the device can consist of a handle (e.g., Alcon-Grieshaber Revolution—DSP™ handle) connected to a small gauge cannula (e.g., 19, 20 or 25 gauge), wherein the inner dimension of the cannula can be used to house an optical fiber assembly comprising one or more, or a plurality of, fiber guides, each comprising one or more custom polymer optical fibers arranged in a specified geometry. The optical fiber assembly contained within the cannula can be connected via a handle mechanism, such as a simple push/pull mechanism, to the handle. The output from a light source, such as a xenon light source, can be optically coupled using standard SMA optical fiber connectors to the proximal end of the optical fiber assembly. The light source light output can be directly coupled to the optical fiber assembly, or an intermediary optical cable can be used between the light source and the optical fiber assembly. Either arrangement will allow for the efficient coupling of light from the light source, through the handle and emanating from the optical fiber assembly at the distal end of the cannula. The light source may be equipped with filters, known to those skilled in the art, to reduce the damaging thermal effects of infrared radiation originating from the light source. Activation of the handle mechanism, such as by a gentle and reversible squeezing action, can cause the fiber guides of the optical fiber assembly to diverge in a predetermined and adjustable manner at the distal end of the cannula. A simple mechanical locking mechanism, as will be known to those in the art, can be used to fix the illumination angle until released and/or readjusted by the user. Light emanating from the optical fiber assembly at the distal end of the cannula can be used to illuminate an area over a solid angle $\Omega$, the angle $\Omega$, being continuously adjustable by the operator via the handle.

One embodiment of the present invention is a surgical illumination system comprising: a light source for providing a light beam; an optical cable, optically coupled to the light source for receiving and transmitting the light beam; a handpiece operably coupled to the optical cable; an optical fiber assembly operably coupled to the handpiece, wherein the optical fiber assembly is optically coupled to the optical cable to receive and transmit the light beam and wherein the optical fiber assembly comprises a plurality of fiber guides, wherein each fiber guide comprises a cladding having one or more fiber cores for transmitting and scattering the light beam to illuminate the surgical field, and a cannula, operably coupled to the handpiece for housing and directing the optical fiber assembly. The surgical illumination system can further comprise a separator operable to maintain a spacing between the fiber guides.

The optical fiber assembly, the cannula, and the handpiece can be fabricated from biocompatible materials. The optical cable can comprise a first optical connector operably and optically coupled to the light source and a second optical connector optically coupled to the handpiece (to optically couple the optical cable to the optical fiber assembly housed within the handpiece and cannula), or a single optical connector to connect the optical cable to the light source. These connectors can be standard SMA optical fiber connectors. The optical fiber assembly optical cores are of a sufficient gauge, as will be known to those familiar in the art, so as to transmit the light beams from the light source to the surgical field.

To enable some of the advantages of the embodiments of this invention, the optical fiber assembly can be operably coupled to the handpiece to enable linear displacement of the optical fiber assembly within the cannula. The handpiece can include an adjustment means, such as a push/pull mechanism, for adjusting the linear displacement of the optical fiber assembly. Other adjusting means as known to those in the art can also be used including, for example, a mechanical coupling, an electrical coupling, a magnetic coupling, a pneumatic coupling or any combination thereof. The distal end (end closest to the surgical field) of the optical fiber assembly can be coincident with an open aperture of the cannula. Adjusting the linear displacement via the adjusting means can thus cause the optical fiber assembly to exit the open aperture by an amount corresponding to the change in linear displacement (a reverse adjustment can retract the optical fiber assembly). Further, a separator can be positioned between the fiber guides in such a way that the fiber guides can be uniformly displaced outward from one another by an amount proportional to the change in linear displacement from the distal end of the cannula. Alternatively, a material such as a memory shape alloy can be incorporated into the cladding of the fiber guides to effectuate the uniform displacement of the fiber guides as they exit the cannula distal end. In this way, the angle of illumination and the amount of illumination provided by the optical fiber assembly from the light beam to illuminate the surgical field (e.g. the retina of an eye) can be adjusted by the surgeon as needed. The embodiments of this invention can provide a range of illumination angles up to about 180° (e.g., 20° to about 180°).

Other embodiments of the present invention can include a method for wide-angle illumination of a surgical field using a multi-fiber variable intensity wide-angle illuminator in accordance with the teachings of this invention, and a surgical handpiece embodiment of the multi-fiber variable intensity wide-angle illuminator of the present invention for use in ophthalmic surgery. The embodiments of this invention can be implemented as a handpiece connected to a cannula or other housing including a fiber optic cable terminating in a multi-fiber optical fiber assembly in accordance with the teachings of this invention. Further, embodiments of this invention can be incorporated within a surgical machine or system for use in ophthalmic or other surgery. Other uses for a multi-fiber variable intensity wide-angle illuminator designed in accordance with the teachings of this invention will be apparent to those familiar with the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings in which like reference numbers indicate like features and wherein.

DETAILED DESCRIPTION OF THE INVENTION

Preferred embodiments of the present invention are illustrated in the FIGURES like numerals being used to refer to like and corresponding parts of the various drawings.

The various embodiments of the present invention provide for a small gauge (e.g., 19, 20, or 25 gauge) optical fiber based endo-illuminator device for use in surgical procedures, such as in vitreo-retinal/posterior segment surgery. Embodiments of this invention can comprise a handpiece, such as the Alcon-Grieshaber Revolution—DSP™ handpiece sold by Alcon Laboratories, Inc., Fort Worth, Tex., connected to a small gauge cannula (e.g., 19, 20, or 25 gauge). The inner dimension of the cannula can be used to house an optical fiber assembly comprising a plurality of fiber guides and a means for separating the plurality of fiber guides, such as a separator, in accordance with the teachings of this invention. Embodiments of the multi-fiber wide-angle illuminator can be configured for use in the general field of ophthalmic surgery. However, it is contemplated and it will be realized by those skilled in the art that the scope of the present invention is not limited to ophthalmology, but may be applied generally to other areas of surgery where wide-angle and/or variable illumination may be required.

An embodiment of the multi-fiber variable-intensity, wide-angle illuminator of this invention can comprise an optical fiber assembly, stem and handpiece fabricated from biocompatible polymeric materials, such that the invasive portion of the wide-angle illuminator is a disposable surgical item. Unlike the prior art, each embodiment of the multi-fiber variable-intensity, wide-angle illuminator of this invention can provide high optical transmission/high brightness with low optical losses. Embodiments of this invention fabricated from biocompatible polymeric materials can be integrated into a low cost, articulated handpiece mechanism, such that these embodiments can comprise an inexpensive disposable illuminator instrument.

Figure 1:
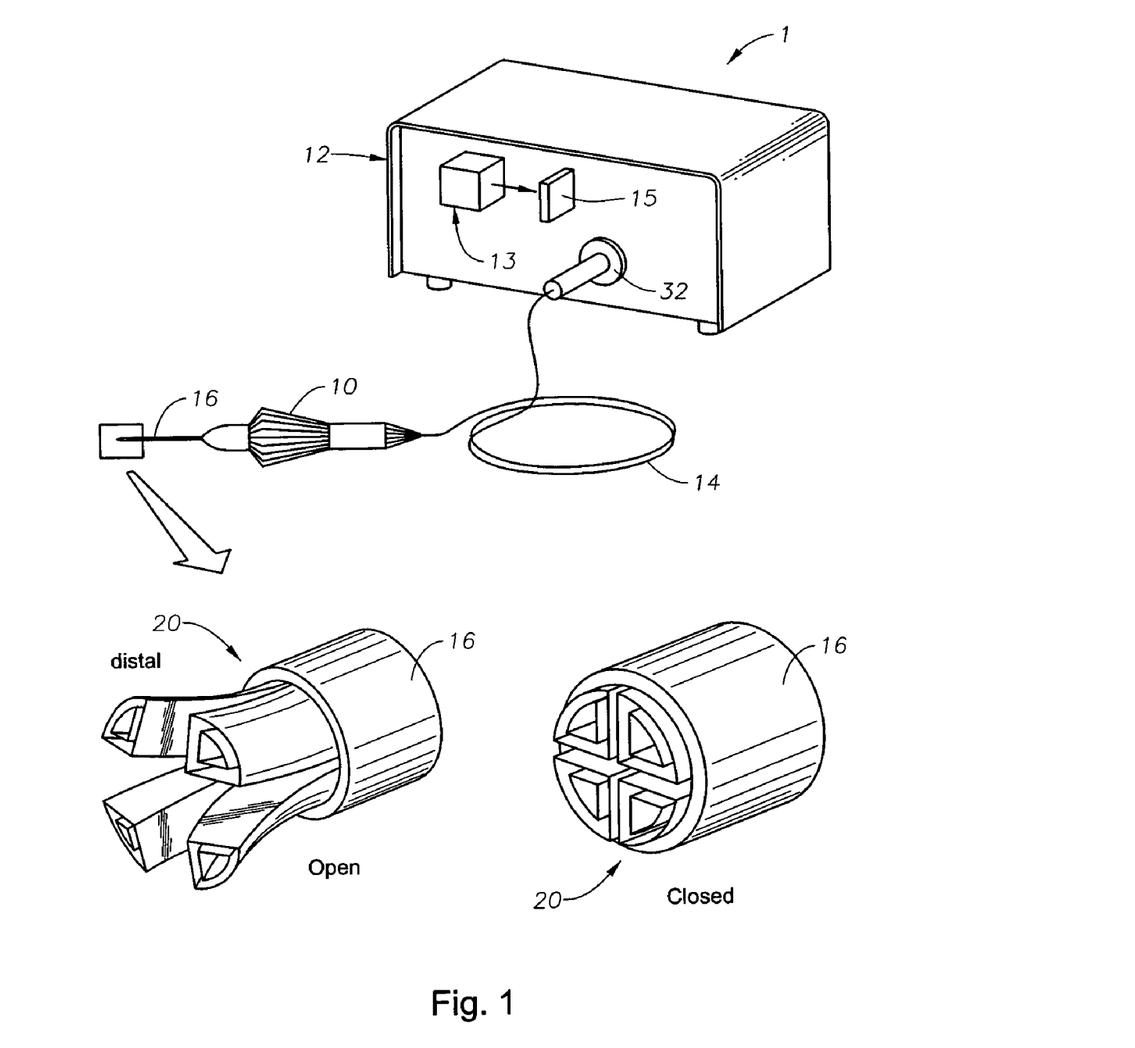
FIG. 1 is a simplified diagram of a surgical illumination system according to one embodiment of this invention.

FIG. 1 is a simplified diagram of a system 1 comprising a handpiece 10 for delivering a beam of light from a light source 12 through cable 14 and a stem (cannula) 16. Cable 14 can be any gauge fiberoptic cable as known in the art, but preferably comprises a 19, 20, or 25 gauge compatible fiber. Further, cable 14 can comprise a single optical fiber or a plurality of optical fibers optically coupled to receive and transmit light from light source 12 to the distal end of stem 16 through handpiece 10. Stem 16 is configured to house an optical fiber assembly 20, as is more clearly illustrated in FIG. 2. A blow-up of one embodiment of optical fiber assembly 20 is included in FIG. 1 to demonstrate the open and closed positions of the optical fiber assembly 20. Coupling system 32 can comprise an optical fiber connector at an end of cable 14 to optically couple light source 12 to optical fiber assembly 20 within handpiece 10, as discussed more fully below.

Figure 2:
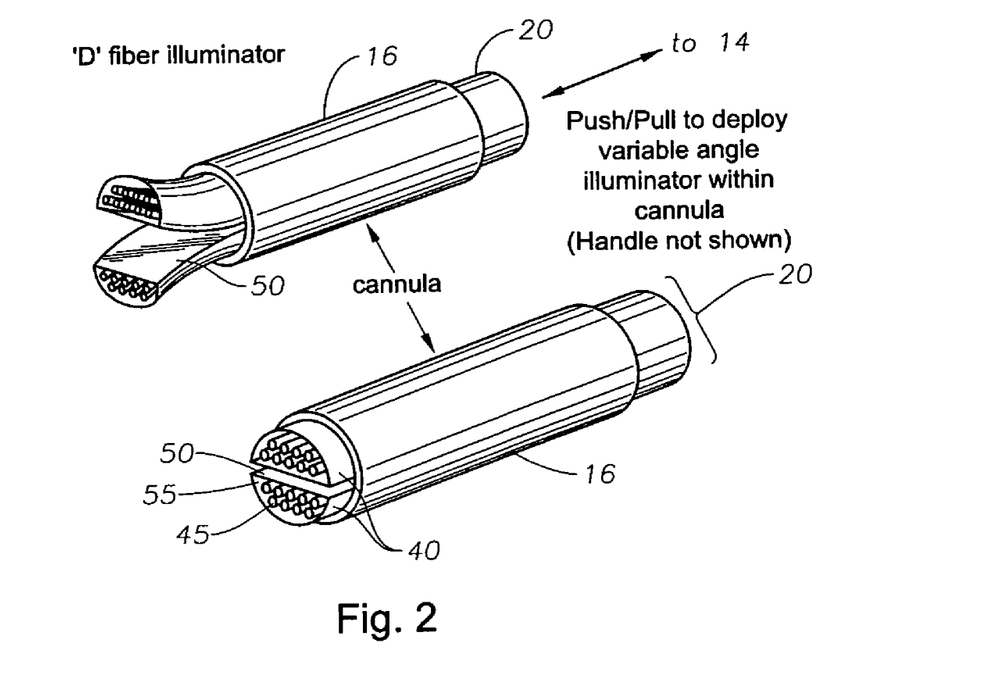
FIG. 2 is a magnified view of the distal end a stem 16 including one embodiment of an optical fiber assembly 20 of the present invention.

FIG. 2 is a magnified view of the distal end of stem 16 including one embodiment of optical fiber assembly 20 of the present invention. Stem 16 is shown housing optical fiber assembly 20. Optical fiber assembly 20 is optically coupled to fiber optic cable 14. In some embodiments an additional optical fiber can be optically coupled between optical fiber assembly 20 and fiber optic cable 14. When implemented, such an additional optical fiber is of a gauge compatible with the gauge of fiber optic cable 14, such that it can receive and transmit light from fiber optic cable 14. Handpiece 10 can be any surgical handpiece as known in the art, such as the Revolution—DSP™ handpiece sold by Alcon Laboratories, Inc. of Fort Worth, Tex. Light source 12 can comprise light element 13, which produces the light beam from light source 12 and which can be a xenon light source, a halogen light source, or any other light source capable of delivering, for example, incoherent light through a fiber optic cable. Stem 16 can be a small gauge cannula, preferably within the range of 18 to 30 gauge, as known to those in the art, and most preferably of 19, 20 or 25 gauge. Stem 16 can be stainless steel or a suitable biocompatible polymer (e.g., PEEK, polyimide, etc.) as known to those in the art and can be consistent with a disposable instrument design.

Figure 9:
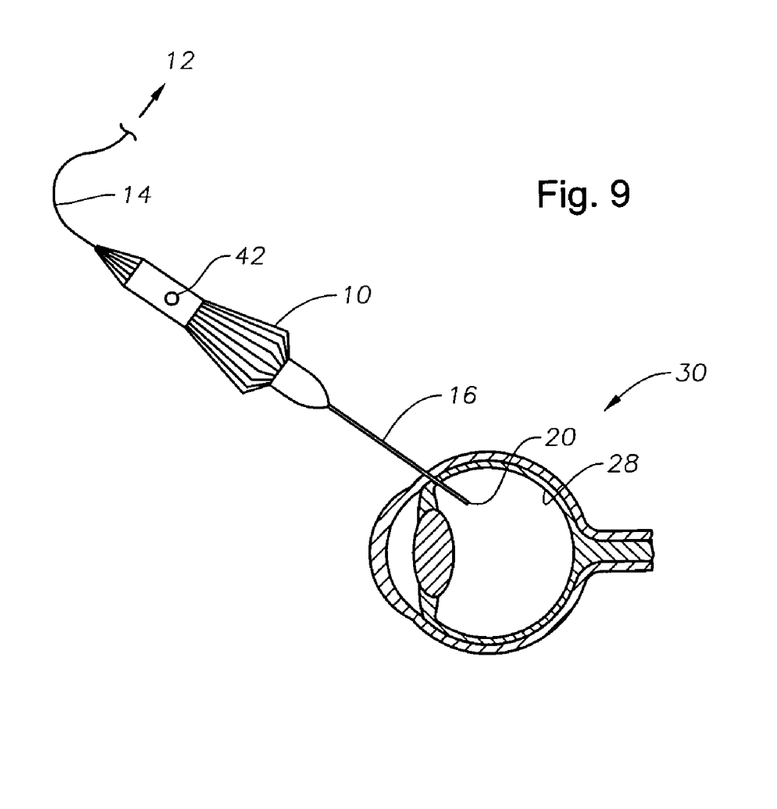
FIG. 9 is an illustration of the use of one embodiment of the illuminator of this invention in an ophthalmic surgery.

The optical fiber assembly 20 or an optional intermediate fiber housed within the stem 16 can be operably coupled to the handpiece 10, for example, via an adjusting means 42, as shown in FIG. 9. Adjusting means 42 can comprise for example, a simple mechanical, magnetic or pneumatic push/pull mechanism as known to those in the art. Light source 12 can be optically coupled to handpiece 10 (i.e., to optical fiber assembly 20) using, for example, standard SMA (Scale Manufacturers Association) optical fiber connectors at the proximal ends of fiber optic cable 14. This allows for the efficient coupling of light from the light source 12 through fiber optic cable 14 to the handpiece 10 and finally emanating from optical fiber assembly 20 at the distal end of the stem 16. Light source 12 may further comprise filters 15, as known to those skilled in the art, to reduce the damaging thermal effects of absorbed infrared radiation originating at the light source. The light source 12 filter(s) can be used to selectively illuminate a surgical field with different colors of light, such as to excite a surgical dye.

Optical fiber assembly 20 can terminate flush with or slightly within the distal end of stem 16. Thus, for example, when not in use, optical fiber assembly 20 can be shielded within stem 16, the distal end of optical fiber assembly 20 being co-incident with the open aperture at the distal end of stem 16. Activation of the adjusting means 42, by, for example, a gentle and reversible sliding action, can cause optical fiber assembly 20 to exit (or retract into) the distal end of stem 16 by an amount determined and adjusted by sliding adjusting means 42. The amount of illumination and the solid angle of illumination may be varied in proportion to the amount of optical fiber assembly 20 that is exposed at the end of stem 16. In this way, a surgeon can adjust the amount of light spread over a surgical field as desired to optimize the viewing field while minimizing glare. The adjusting means 42 of handpiece 10 can be any adjusting means as known to those familiar with the art, and can include a mechanical, electro-mechanical, pneumatic or magnetic coupling and actuations mechanism.

In one embodiment of the multi-fiber variable-intensity, wide-angle illuminator of the present invention, a simple mechanical locking mechanism, as known to those skilled in the art, can permit the illumination angle to be fixed, until released and/or re-adjusted by the user via the adjusting means 42. Light emanating from the distal end of stem 16 will illuminate an area over a solid angle θ, the angle θ being capable of continuous adjustment by a user (e.g., a surgeon) via the adjusting means 42 of handpiece 10 (i.e., as more of optical fiber assembly 20 is exposed past the distal end of stem 16, the greater the solid angle θ, and vice versa).

In the embodiment of FIG. 2, the optical fiber assembly 20 comprises a pair of "D"-shaped fiber guides 40. Each hemispherical "D" fiber guide 40 can comprise a single or a plurality of polymer wave-guide fiber cores 45. The shape of the fiber cores 45 may be a circular cross section, as shown in FIG. 2, although other shapes may be used without departing from the general scope of this invention. The pair of "D" fiber guides 40 are fabricated such that each hemispherical fiber guide 40 fits within the stem 16 such that a mechanical means of separation 50 (hereafter referred to as a "separator" 50) is positioned between the fiber guides 40 and operably coupled to maintain a separation between fiber guides 50 and to allow fiber guides 50 to diverge, in a uniform and controlled manner as adjusting means 42 is activated to cause optical fiber assembly 20 to exit the distal end of stem 16. Conversely, fiber guides 40 can be caused to converge when optical fiber assembly 20 is retracted into the distal end of stem 16 by activation of adjusting means 42.

Separator 50 can be made, for example, from an elastic material such as silicon. Alternatively, a separator 50 can comprise polyurethane or viscoelastic material in various shapes (e.g., a sphere) positioned between fiber guides 40. In still another embodiment, separator 50 can comprise a shape memory alloy, such as Nitinol, either operably coupled to or integrated into each fiber guide 40 and configured to diverge the fiber guides in the same uniform manner previously described upon sliding out of the distal end of stem 16. The shape memory alloy can be manufactured for this purpose in a manner known to those familiar with the art. Note that in a multiple fiber guide 40 embodiment of the illuminator of this invention, the distance between the various fiber guides 40 can be equal, or unequal, depending on the illumination pattern desired. Radial symmetry of the illumination can thus be preserved entirely, or along different angular directions.

Figure 3:
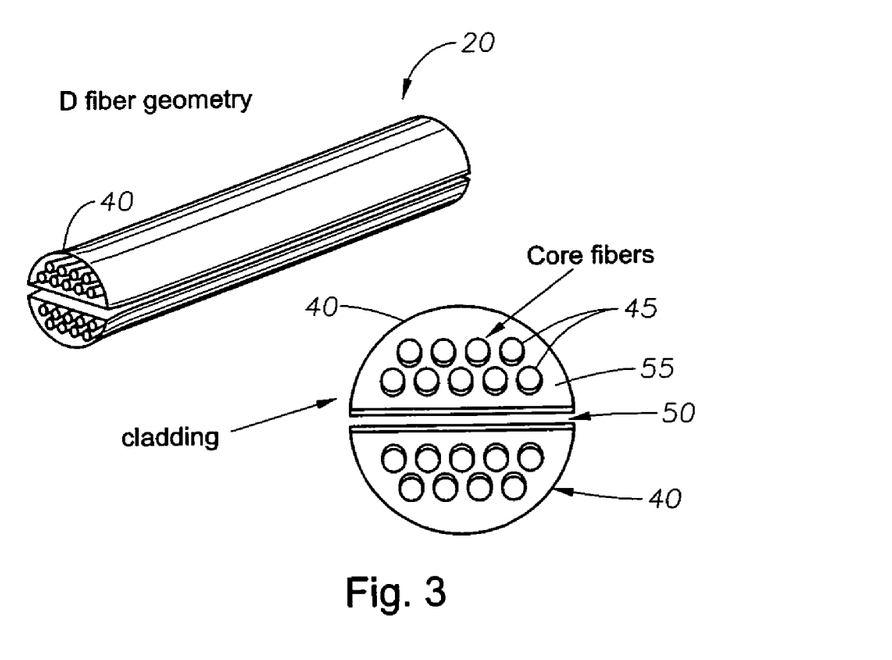
FIG. 3 is a simplified block diagram illustrating the optical fiber assembly 20 of the embodiment of FIG. 2.

FIG. 3 is a simplified block diagram illustrating the optical fiber assembly 20 of the embodiment of FIG. 2. The construction of the optical fiber assembly 20 is such that a cladding material 55, having a low refractive index, surrounds the higher refractive index polymer wave-guide fiber cores 45, thereby confining the light beam from the light source 12, by optical principles well known to those familiar with the art. In order to maximize the optical light throughput of the illuminator of this invention and the illumination angle achieved, it is desirable to employ a large difference in refractive index between the fiber cores 45 and the cladding material 55. For example, a fluorocarbon polymer can be used for the cladding material 55 and a material such as polystyrene can be used for the fiber core 45 material.

Figure 4:
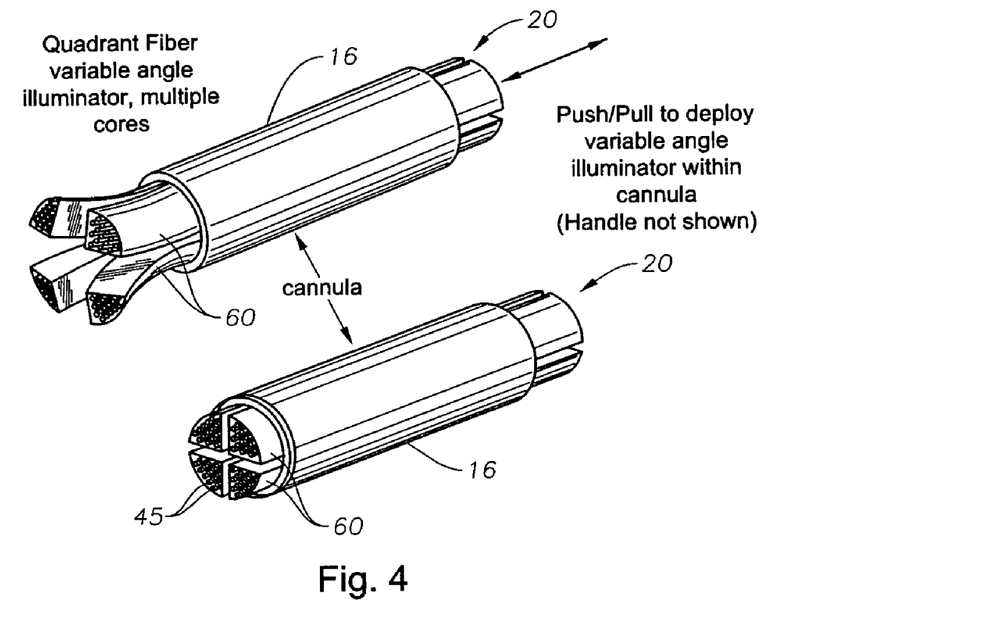
FIG. 4 is a simplified diagram illustrating another embodiment of the wide-angle illuminator of the present invention.

FIG. 4 is a simplified diagram illustrating another embodiment of the multi-fiber variable intensity wide-angle illuminator of the present invention. In this embodiment, four equally sized quadrant fiber guides 60 are configured symmetrically within stem 16. Each quadrant fiber guide 60 can contain a single polymer wave-guide fiber core 45 or a plurality of polymer wave-guide fiber cores 45, as shown in FIG. 4. Quadrant fiber guides 60 are contained within a stem (cannula) 16 as in the embodiment of FIG. 2.

Figure 5:
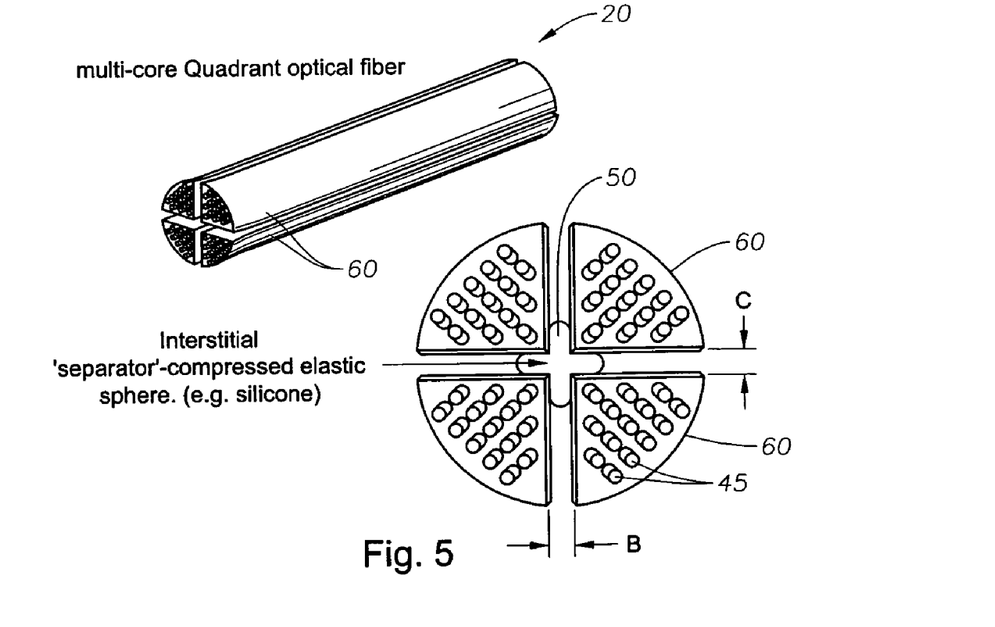
FIG. 5 is an illustration of an interstitial separator 50 configured to fit centrally between fiber guides 60 according to one embodiment of this invention.

FIG. 4 shows this embodiment of the multi-fiber variable intensity wide-angle illuminator of the present invention in both retracted and extended positions. The operation of the embodiment of FIG. 4 is conceptually the same as that of the embodiment of FIG. 2. As shown more clearly in FIG. 5, an interstitial separator 50 can be configured to fit centrally between the fiber guides 60. Interstitial separator 50 can be, for example, a compressed elastic sphere made of silicone. It will be apparent to those skilled in the art that any number of optical fiber guides 60, each containing one or more polymer wave-guide fiber cores 45 may be employed in the various embodiments of this invention, in order to achieve the same variable angle illumination effect. Furthermore, it is to be appreciated that the shape of the fiber cores 45 may be a circular cross section, such as in FIGS. 2-5, or of any other cross-sectional shape, without departing from the scope of the present invention.

Figure 6:
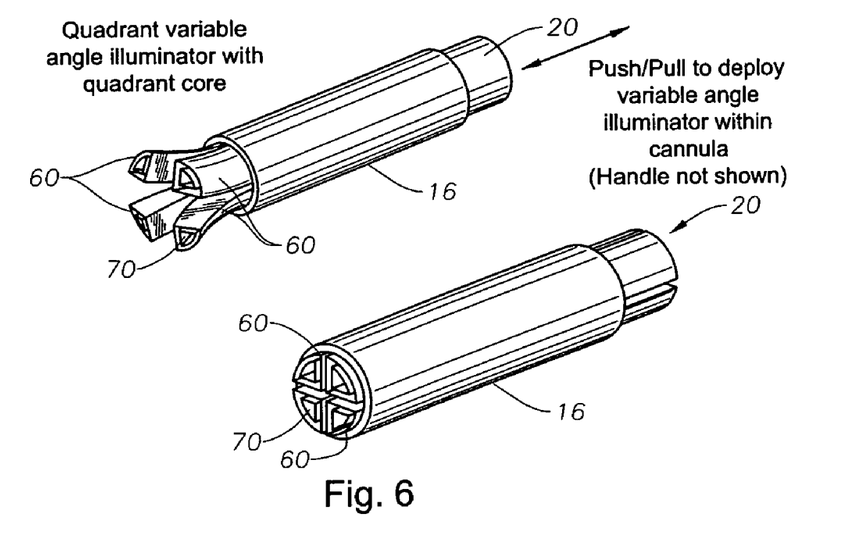
FIGS. 6 and 7 are simplified drawings showing additional embodiments of the illuminator of this invention.
Figure 7:
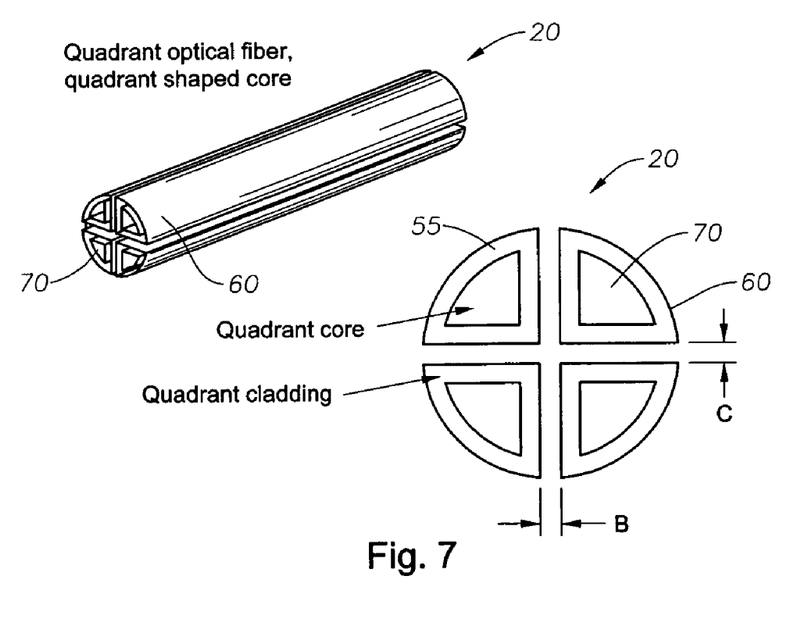

FIGS. 6 and 7 show an additional embodiment of the multi-fiber variable intensity wide-angle illuminator of this invention. This embodiment comprises four quadrant fiber guides 60, as in the embodiment of FIGS. 4 and 5. However, fiber cores 70 are single fiber cores having a quadrant (¼ circle) shaped cross-section. The operation and performance of this embodiment is similar to that of the embodiments previously described.

In order to maximize the optical light throughput and the illumination angle achieved by the embodiments of the present invention, it is desirable to employ a fiber core 40 or fiber cores 40 having a large numerical aperture and preferably as large as practical numerical aperture. The numerical aperture ("NA") is a fiber optic parameter determined from the refractive index ($N_{core}$) of the fiber core material and the refractive index ($N_{clad}$) of the cladding material and is given by the equation $$NA = n_0 \sin(\alpha) = (n^2_{core} - n^2_{clad})^{1/2}.$$

Where "α" is the acceptance half-angle at which light sent into the fiber core 45 will be guided, and $n_0$ is the refractive index of the medium (cladding 55) surrounding the optical fiber core 45. The launch condition for the light guided by the fiber cores 45 will be set within the external light source 12 component. A fiber core 45 and cladding 55, fabricated from, for example, polystyrene ("PS", $n_{core}=1.59$) and polyfluoroethylene ("PFE", $n_{clad}=1.32$), will result in a high numerical aperture of approximately 0.9. This translates into an acceptance angle (in vacuo) of 64°. Below are provided some example calculations of the fiber optic light carrying capacity (brightness/luminosity) for the 20 gauge Alcon bullet probe wide-angle illuminator fiber and for a 20 gauge multiple shaped fiber embodiment of the illuminator of the present invention. The purpose is to compare and illustrate the potential light carrying capacity of the present invention as greatly improved over the prior art.

---

20 Gauge Alcon Bullet Probe Wide-Angle Illuminator Fiber* acrylic core/fluoropolymer cladding

Total fiber diameter = 0.762 mm
Total core diameter = 0.736 mm

Numerical Aperture = 0.628

The brightness or luminosity B that can be carried by an optical fiber can be approximated by the following equation.

$$B = (NA)^2 \, S \, 10^{(\alpha L/10)}$$

Where S = (area of core/total fiber area) = 0.93, α = 0.25 db/m.
α is the optical attenuation in dB/m, and L is the length of the fiber in meters (1 m)

Therefore, $B_{Alcon} = 0.388$

---

20 Gauge Multiple Shaped Fiber Illuminator (single core design)

(only 1 of 4 fiber quadrants shown)
polystyrene core/fluoropolymer cladding

Total quadrant radius = 0.3935 mm (×4)
Total core diameter = 0.110 mm (×4)

Numerical Aperture = 0.628

$$B = (NA)^2 \, S \, 10^{(\alpha L/10)}$$

Where S = (area of core/total fiber area) = 0.78, α = 0.20 dB/m
α is the optical attenuation in dB/m, and L is the length of the fiber in meters (1 m)

Therefore, $B_{MSFI} = 0.598$, showing that the potential light carrying capacity of the embodiments of the present invention can be ~50% greater than, for example, the Alcon bullet probe.

*Calculation is for fiber only and does not account for losses due to presence of bullet probe termination

---

Returning now to the embodiments of FIGS. 2-7, the various embodiments can be implemented, for example, to fit within a 19, 20, or 25 gauge cannula (stem 16). Further, the dimensions illustrated as B and C between the quadrant fibers of FIG. 5 can be such that the distribution of light exiting from the fiber cores 45 will be radially symmetric, so long as the gap represented by dimensions B and C are equal (B=C). Other illumination profiles may be created where B≠C.

Figure 8:
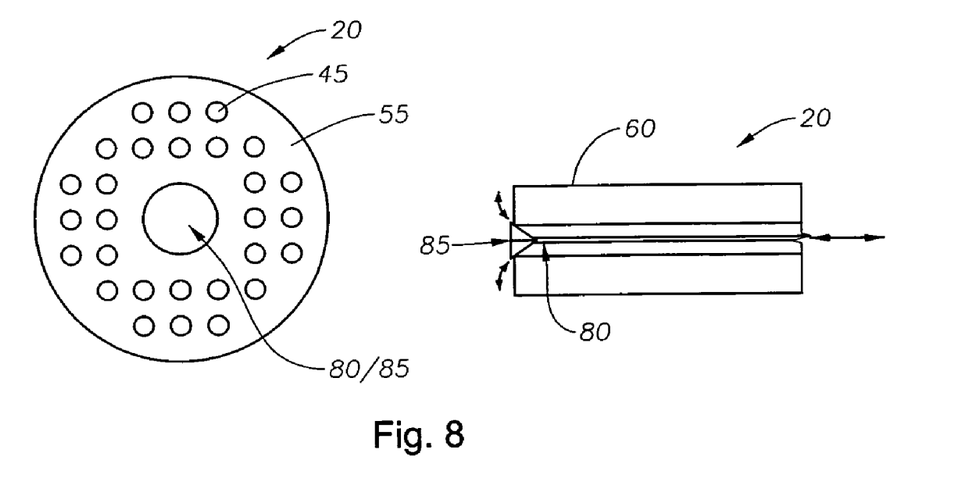
FIG. 8 is an illustration of yet another embodiment of the present invention in which optical fiber assembly 20 comprises a central rod 80 surrounded by cladding 55 containing fiber cores 45.

FIG. 8 shows yet another embodiment of the present invention in which optical fiber assembly 20 comprises a central rod 80 surrounded by cladding 55 containing the fiber cores 45. The embodiment of FIG. 8 can be operated to flare the fiber cores 45 in a manner analogous to the multiple fiber-guide embodiments of this invention (e.g., the rod is displaced along the central axis of the optical fiber assembly 20 and is operable to move linearly with respect to the cladding 55 and to flare the cladding 55 so as to change the illumination angle of the fiber cores 45 in proportion to the rod's linear movement) and provide a continually variable angle of illumination by, for example, having a plunger type mechanism (rod 80) that, when the optical fiber assembly 20 is pushed or pulled by a simple push/pull mechanism within the handle 10, is operable to flare the tip of the optical fiber assembly 20 at the distal end of the cannula due to the action of the larger diameter plunger head 85 of rod 80.

FIG. 9 illustrates the use of one embodiment of the multi-fiber variable-intensity, wide-angle illuminator of this invention in an ophthalmic surgery. In operation, handpiece 10 delivers a beam of spatially and temporally incoherent light having a broad spectral bandwidth through stem 16 via optical fiber assembly 20 to illuminate a retina 28 of an eye 30. The collimated light delivered through handpiece 10 to optical fiber assembly 20 is generated by light source 12 and delivered to illuminate the retina 28 by means of fiber optic cable 14 and coupling system 32. Optical fiber assembly 20 spreads the light beam delivered from light source 12 over as large an area of the surgical field as, for example, a microscopic wide-angle objective lens permits a surgeon to see.

An advantage of the optical fiber assembly 20 and of the embodiments of the multi-fiber, variable-intensity wide-angle illuminator of this invention, is that an operator can continuously vary the intensity and angle of illumination of the light exiting optical fiber assembly 20 to optimize viewing conditions within the surgical field. The light emanating from optical fiber assembly 20 can thus be spatially dispersed and controlled as desired by the operator (e.g., surgeon). The embodiments of the multi-fiber, variable-intensity wide-angle illuminator of the present invention are thus operable to adjust the angle and intensity of the light provided by light source 12 to substantially cover the area of the surgical field desired by a surgeon.

The embodiments of the multi-fiber variable-intensity, wide-angle illuminator of this invention provide several other advantages over the prior art, such as maximizing light transmission by eliminating the requirement of multiple transmitting, reflecting, or diffracting optical elements, all of which can present sources of further transmission loss between a light source 12 and a target area to be illuminated. Furthermore, the embodiments of this invention have an inherently high light flux capacity and a variable illumination angle, which will permit the operator to tailor the angular illumination requirements for a specific surgical environment. Additionally, a variable illumination angle allows an operator to adjust the intensity of the illumination using both source intensity variations and angle of incidence variations to minimize glare and shadowing in the surgical field. By varying the angle of illumination on a specific portion of the surgical field, an operator, such as a surgeon, can get an improved perception of spatial awareness.

A traditional fiber-optic illuminator with a polished face will produce an included illumination angle that is a function of the numerical aperture ("NA") of the fiber. NA defines the acceptance angle of entrance of the light from the light source into the fiber optic cable. Commonly, the fiber used for ophthalmic illumination applications has a typical NA of 0.5. This provides a calculated acceptance angle of 60° in vacuo. Wide-angle viewing systems commonly used by ophthalmic surgeons typically have a viewing angle requirement of greater than about 100° in vivo. Thus, conventional fiber optic illuminators cannot provide a lighted field that matches the viewing system angle of visibility. The embodiments of the variable-intensity, wide-angle illuminator of this invention can provide an angle of illumination in excess of about 180° (i.e., a range of illumination angles up to about 180°).

The embodiments of the present invention differ from the prior art in that they offer a means of achieving a wide and variable angle illumination probe exhibiting low optical losses and having a high optical transmission/high brightness. The embodiments of this invention can also be fabricated from biocompatible polymeric materials, and can be integrated into a low cost articulated handle mechanism rendering the device a good candidate for a disposable illuminator instrument. Although the embodiments of the present invention have been described and particular reference to the general area of ophthalmic surgery, the teachings contained herein can apply equally wherever it is desirous to provide variable angle illumination, and a transparent fluid might interfere with the ability to obtain wide angle illumination.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide wide-angle and variable illumination, and where contact with a transparent fluid might normally interfere with the ability to obtain wide-angle illumination.

What is claimed is:

1. An illuminator, comprising:
   a handpiece, operably coupled to an optical cable, wherein the optical cable is operable to be optically coupled to a light source for receiving and transmitting a light beam from the light source;
   an optical fiber assembly, operably coupled to the handpiece, wherein the optical fiber assembly is optically coupled to the optical cable to receive and transmit the light beam, and wherein the optical fiber assembly comprises a plurality of fiber guides, wherein each fiber guide comprises a cladding having a plurality of fiber cores for transmitting and scattering the light beam to illuminate a surgical field; and
   a cannula, operably coupled to the handpiece, for housing and directing the optical fiber assembly.

2. The illuminator of claim 1, further comprising a separator operable to maintain a spacing between the fiber guides.

3. The illuminator of claim 2, wherein the separator is a polyurethane or viscoelastic separator.

4. The illuminator of claim 2, wherein the separator is made of a shape memory alloy.

5. The illuminator of claim 1, wherein the optical fiber assembly is operable to extend beyond the distal end of the cannula, and wherein the fiber guides are operable to diverge from one another in proportion to the amount the optical fiber assembly extends beyond the distal end of the cannula so as to vary the angle of illumination of the light beam provided by the fiber cores.

6. The illuminator of claim 1, wherein the optical fiber assembly is compatible with and sized to fit within a 19, 20 or 25 gauge cannula.

7. The illuminator of claim 1, wherein the cannula and the handpiece are fabricated from biocompatible materials.

8. The illuminator of claim 1, wherein the optical cable is optically coupled at a distal end to the optical fiber assembly and at a proximal end to the light source, and wherein the optical cable comprises an optical connector at the proximal end.

9. The illuminator of claim 1, wherein the plurality of fiber guides comprises two "D"-shaped fiber guides.

10. The illuminator of claim 1, wherein the plurality of fiber guides comprises four quadrant-shaped fiber guides.

11. The illuminator of claim 1, wherein the optical fiber assembly is operably coupled to the handpiece to enable linear displacement of the optical fiber assembly within the cannula.

12. The illuminator of claim 11, further comprising a means for adjusting the linear displacement of the optical fiber assembly.

13. The illuminator of claim 12, wherein the means for adjusting comprises at least one means selected from the group consisting of an electro-mechanical actuator, a pneumatic actuator, an electric actuator and a magnetic actuator.

14. The illuminator of claim 12, wherein the means for adjusting comprises a push-pull mechanism.

15. The illuminator of claim 11, wherein changing the linear displacement causes the optical fiber assembly to change position relative to a distal end of the cannula, in either a proximal or a distal direction.

16. The illuminator of claim 15, wherein the position of the optical fiber assembly relative to the distal end of the cannula determines an angle of illumination and an amount of illumination provided by the optical fiber assembly to illuminate the surgical field.

17. The illuminator of claim 1, wherein the light beam comprises a beam of relatively incoherent light.

18. The illuminator of claim 1, wherein the light source is a xenon light source.

19. An illuminator, comprising:
a handpiece, operably coupled to an optical cable, wherein the optical cable is operable to be optically coupled to a light source for receiving and transmitting a light beam from the light source;
an optical fiber assembly, operably coupled to the handpiece, wherein the optical fiber assembly is optically coupled to the optical cable to receive and transmit the light beam, and wherein the optical fiber assembly comprises a fiber guide, wherein the fiber guide comprises a cladding having one or more fiber cores for transmitting and scattering the light beam to illuminate a surgical field, and a rod, displaced along the central axis of the optical fiber assembly and operable to move linearly with respect to the cladding and to flare the cladding so as to change the illumination angle of the fiber cores in proportion to the rod's linear movement; and
a cannula, operably coupled to the handpiece, for housing and directing the optical fiber assembly.

20. A surgical illumination system comprising:
a light source for providing a light beam;
an optical cable, optically coupled to the light source for receiving and transmitting the light beam;
a handpiece, operably coupled to the optical cable;
an optical fiber assembly, operably coupled to the handpiece, wherein the optical fiber assembly is optically coupled to the optical cable to receive and transmit the light beam, and wherein the optical fiber assembly comprises a plurality of fiber guides, wherein each fiber guide comprises a cladding having a plurality of fiber cores for transmitting and scattering the light beam to illuminate a surgical field; and
a cannula, operably coupled to the handpiece, for housing and directing the optical fiber assembly.

21. The surgical illumination system of claim 20, further comprising a separator operable to maintain a spacing between the fiber guides.

22. The surgical illumination system of claim 21, wherein the separator is a polyurethane or viscoelastic separator.

23. The surgical illumination system of claim 21, wherein the separator is made of a shape memory alloy.

24. The surgical illumination system of claim 20, wherein the optical fiber assembly is operable to extend beyond the distal end of the cannula, and wherein the fiber guides are operable to diverge from one another in proportion to the amount the optical fiber assembly extends beyond the distal end of the cannula so as to vary the angle of illumination of the light beam provided by the fiber cores.

25. The surgical illumination system of claim 20, wherein the optical fiber assembly is compatible with and sized to fit within a 19, 20 or 25 gauge cannula.

26. The surgical illumination system of claim 20, wherein the cannula and the handpiece are fabricated from biocompatible materials.

27. The surgical illumination system of claim 20, wherein the optical cable is optically coupled at a distal end to the optical fiber assembly and at a proximal end to the light source, and wherein the optical cable comprises an optical connector at the proximal end.

28. The surgical illumination system of claim 20, wherein the plurality of fiber guides comprises two "D"-shaped fiber guides.

29. The surgical illumination system of claim 20, wherein the plurality of fiber guides comprises four quadrant-shaped fiber guides.

30. The surgical illumination system of claim 20, wherein the optical fiber assembly is operably coupled to the handpiece to enable linear displacement of the optical fiber assembly within the cannula.

31. The surgical illumination system of claim 30, further comprising a means for adjusting the linear displacement of the optical fiber assembly.

32. The surgical illumination system of claim 31, wherein the means for adjusting comprises at least one means selected from the group consisting of an electro-mechanical actuator, a pneumatic actuator, an electric actuator and a magnetic actuator.

33. The surgical illumination system of claim 31, wherein the means for adjusting comprises a push-pull mechanism.

34. The surgical illumination system of claim 30, wherein changing the linear displacement causes the optical fiber assembly to change position relative to a distal end of the cannula, in either a proximal or a distal direction.

35. The surgical illumination system of claim 34, wherein the position of the optical fiber assembly relative to the distal end of the cannula determines an angle of illumination and an amount of illumination provided by the optical fiber assembly to illuminate the surgical field.

36. The surgical illumination system of claim 20, wherein the light beam comprises a beam of relatively incoherent light.

37. The surgical illumination system of claim 20, wherein the light source is a xenon light source.

* * * * *

UNITED STATES PATENT AND TRADEMARK OFFICE
CERTIFICATE OF CORRECTION

PATENT NO. : 7,618,177 B2  Page 1 of 1
APPLICATION NO. : 11/410419
DATED : November 17, 2009
INVENTOR(S) : Karl Cazzini It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 397 days.

Signed and Sealed this

Nineteenth Day of October, 2010

David J. Kappos
*Director of the United States Patent and Trademark Office*